United States Patent [19]

Verbeeck

[11] 3,935,256

[45] Jan. 27, 1976

[54] PROCESS FOR THE PRODUCTION OF THE CALCIUM SALT OF PANTOTHENIC ACID

[75] Inventor: John F. Verbeeck, Libertyville, Ill.

[73] Assignee: Thompson-Hayward Chem. Co., Kansas City, Kans.

[22] Filed: Sept. 6, 1974

[21] Appl. No.: 503,796

[52] U.S. Cl. .................... 260/534 A; 260/534 C
[51] Int. Cl.$^2$.................. C07C 99/04; C07C 99/10
[58] Field of Search ................ 260/534 A, 534 C

[56] References Cited
UNITED STATES PATENTS

| | | | |
|---|---|---|---|
| 2,809,213 | 10/1957 | Lekberg et al.................. | 260/534 A |
| 3,564,052 | 2/1971 | Freed............................. | 260/534 A |

Primary Examiner—Richard L. Raymond
Attorney, Agent, or Firm—K. M. Le Fever

[57] ABSTRACT

An improved process for the preparation of dl-calcium pantothenate is described wherein an anhydrous calcium salt of B-Alanine in methanolic solution is reacted with dl-pantolactone directly in a one-step process. The salt of B-Alanine is prepared by reacting acrylonitrile with ammonia, the B-amino-propionitrile formed is hydrolyzed in 50% sodium hydroxide and the sodium salt reacted with a solution of calcium chloride in a liquid which will form an azeotropic mixture with water, any excess sodium hydroxide is neutralized with hydrochloric acid and the water removed by an azeotropic distillation. The reaction mixture is then taken up in methanol and reacted with the dl-pantolactone directly.

3 Claims, No Drawings

PROCESS FOR THE PRODUCTION OF THE CALCIUM SALT OF PANTOTHENIC ACID

BACKGROUND OF INVENTION

One useful growth promoting factor for many types of animals is pantothenic acid, Vitamin ($B_5$), and in a stable and preferred form is used as its double calcium salt, calcium pantothenate. As such it is used in large quantities in animal feeds, encapsulated in multivitamin capsules, and the like.

The classical procedure for the preparation of this valuable material is described by Stiller et al in the Journal of the American Chemical Society 62 1785 (1940) and involves the reaction of isobutyraldehyde with formalin in the presence of potassium carbonate. The aldol product is then purified by distillation and the racemic lactone is formed from the aldol by reaction with sodium bisulfite and potassium cyanide. The pantothenic acid is then formed by coupling the lactone with the ethyl ester of Beta-alanine.

Due to the commercial importance of pantothenic acid and its salts, particularly the calcium double salt, a great deal of research and development effort has gone into methods to improve purity and yields.

U.S. Pat. No. 2,780,645 describes a method for the preparation of calcium dl-pantothenate by reacting 2,4-dihydroxy-3,3-dimethylbutyronitrile with beta-alanine and calcium hydroxide in a lower aliphatic alcohol. U.S. Pat. No. 2,809,213 teaches the preparation of Calcium Pantothenate by reacting beta-alanine and alpha-hydroxy-beta, beta-dimethyl-gamma-butyrolactone (dl-pantolactone) in the presence of a secondary or tertiary amine and calcium metal.

Salts of pantothenic acid are prepared by a process which comprises contacting in a lower alkanol a complex of 1-Brucine and alpha-hydroxy-beta, beta-dimethyl-gamma-butyrolactone and an alkali or alkaline earth metal salt of beta-alanine in U.S. Pat. No. 3,150,175. U.S. Pat No. 3,564,052 teaches the preparation of calcium pantothenate by reacting beta-alanine and pantoyl lactone in the presence of calcium carbide.

BRIEF DESCRIPTION OF INVENTION

It has now been found, and forms the object of this invention, that calcium pantothenate can be formed by a simple and more direct procedure than those taught in the prior art to obtain higher yields of a purer product.

Briefly the invention comprises the steps of reacting dl-pantolactone directly with a substantially anhydrous calcium double salt of beta-alanine in a methanolic solution.

The gist of the invention lies in the preparation of the substantially anhydrous salt of beta-alanine and depends upon distillation of an azeotropic mixture of water, a step which is not taught or described in the prior art.

The process of the invention has the added advantage of being capable of being carried out in a single vessel available in the usual chemical manufacturing plant with a minimum of materials handling steps.

DETAILED DESCRIPTION OF INVENTION

The improved process of the invention may conveniently be divided into a series of steps, as follows:

Step 1. Preparation of Beta-Aminopropionitrile

I. $CH_2=CH-CN$ + $NH_3$ $\longrightarrow$ $H_2N-CH_2-CH_2-CN$
(acrylonitrile)   (Ammonia)   (Beta-aminopropionitrile)

This step is preferably carried out by reacting an aqueous solution, say 20%–30%, of ammonia with acrylonitrile at a temperature of from about 100° to 110°C. until the reaction is complete, normally in from about 5–10 hours.

The Beta-aminopropionitrile is then separated by distillation at about 60°–65° C., preferably at subatmospheric pressures in the order of from about 75–85 mm/Hg.

Step 2. Hydrolysis of Beta-aminopropionitrile to the Sodium salt of Beta-alanine.

II. $H_2N-CH_2-CH_2-CN$ + NaOH $\longrightarrow$ $H_2N-CH_2-CH_2COONa$
(Beta-aminopropionitrile)   (Sodium Hydroxide)   (Sodium-Beta-Alaninate) + $NH_3$ (Ammonia)

The hydrolysis step is preferably carried out by gradually adding to a solution of sodium hydroxide the distilled Beta-aminopropionitrile at a temperature of about 65°–95° C. with stirring and maintaining the reaction time at one within a range of from 0.5–4 hours.

The sodium hydroxide solution is preferably a 50% solution, but one within a range of from about 20–60% may be used. There should be added about a 10–15% stoichemetric excess of sodium hydroxide at this step in order to insure completion of the reaction.

After the reaction is completed, the temperature of the reaction vessel is raised to about 95° to 105° C. at atmospheric pressure to remove approximately 95% of the water present.

Step 3. Preparation of the calcium salt of Beta-Alanine.

III. $2H_2N-CH_2 COONa$ + $CaCl_2$ $\longrightarrow$ $(H_2N-CH_2 CH_2 COO)_2 Ca$ + 2 NaCl
(Sodium-Beta-Alaninate)   (Calcium chloride)   (calcium Beta-Alaninate)   (sodium chloride)

A solution of 98–99% Calcium Chloride in a liquid which forms an azeotrope with water. Liquids which will form such an azeotrope mixture with water, which have no adverse effect on the reaction and which do not contaminate the final product include propanol, isopropanol, isobutanol, 1-butanol, 2-butanol, benzyl alcohol, n-hexane, and the like. Especially preferred, and utilized in the preferred embodiment is a completely denatured ethanol (containing, e.g. 10% methanol, 1% gasoline, 1% methyl butyl ketone and 1% methal acetate) is prepared by admixing 1 part of the calcium chloride in two parts of the denatured alcohol. This solution is added to the sodium salt of beta-alanine prepared as described in Step 2 above and stirred for from 0.5 to 3 hours at 60°–70° C.

The excess of sodium hydroxide is then neutralized with 1 N HCl and the resulting reaction mixture contains the double calcium salt of beta-alanine, sodium chloride, ethanol and water.

Step 4. Distillation of Water-Azeotropic Mixture

Removal of the water present in the reaction mixture, one serious drawback in prior art processes, is simply and efficiently carried out in this step, for example, if ethanol is used, by raising the temperature of the reaction vessel to 78.2° C. the boiling point of the ethanol-water azeotrope, for a period of time sufficient to completely remove the azeotrope. When this is accomplished, the temperature is then raised to about 79° to 80° C. and the residual ethanol is driven off, leaving a semi-solid mixture of calcium beta-alaninate and sodium chloride. This solid is then taken up in methanol, commercial grade, anhydrous, at a ratio of two parts to methanol per part of solid, and filtered to remove crystalline sodium chloride, leaving a methanolic solution of the anhydrous calcium salt of beta-alanine. This may be vacuum dried, after distilling off the methanol, if desired, for uses other than in the preparation of calcium pantothenate. Step 5. Formation of dl-Calcium Pantothenate.

After the ammonia was removed, vacuum was applied to the flask (80 mm Hg.) and water was removed, the temperature being maintained at 50°–60° C.

The residue in the flask, Beta-aminopropionitrile was then distilled at 40 mm/Hg. at 40° to 60° C. in a water bath and a yield of 62%, based on acrylonitrile, of product was obtained.

Step 2. Hydrolysis of Beta-Aminopropionitrile to the Sodium Salt of Beta-Alanine In a 3-liter round bottomed flask equipped with 3 necks fitted with a stirrer, a thermometer and a separatory funnel, and in a Glass Col mantle, there was introduced 5.0785 mols of sodium hydroxide in the form of a 50 percent aqueous solution. The sodium hydroxide was heated to 65° C. and 4.6168 mols of the Beta-aminopropionitrile, prepared as described in Step 1 above, was introduced dropwise via the separatory funnel at such a rate that the temperature did not raise above 80° C. The addition took about 40 minutes and when completed the mixture was heated to 95° C. and maintained at that temperature with stirring for 1 hour. After that time the reaction was completed as shown by thin layer chromatography.

Excess sodium hydroxide (0.46168 mols) was neutralized by 1 N hydrocholoric acid and 95–97% of the water present was distilled off (Carl-Fischer analysis).

Step 3. Preparation of the Calcium Salt of Beta-Alanine

To a 5 liter flask in a Glass Col mantle fitted with a

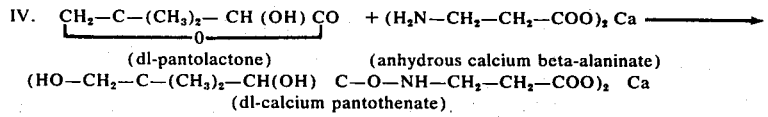

IV. 
(dl-pantolactone)    (anhydrous calcium beta-alaninate)
(HO—CH$_2$—C—(CH$_3$)$_2$—CH(OH)  C—O—NH—CH$_2$—CH$_2$—COO)$_2$ Ca
(dl-calcium pantothenate)

Commercially available dl-pantolactone of about 98% purity as a 70% solution in methanol is admixed with a methanoloic solution of the calcium salt of beta-alanine prepared as described in Step 4 above. The reaction is maintained at a temperature of about 55° to 65° for from about 6–9 hours. The reaction product is cooled, filtered, the methanol evaporated and the resulting calcium pantothenate recovered at a yield of about 95.8%, based on the starting pantolactone. This compares very favorably with the 90–91% yields reported by prior art techniques.

The invention will be more clearly explained by reference to the following specific example.

Step 1. Preparation of Beta-Aminopropionitrile

Following the classical procedure (ORGANIC SYNTHESIS-COLLECTIVE VOLUME II — HORNING, John Wiley & Sons, Inc., New York 1955) Beta-aminopropionitrile was prepared as follows:

To a 3-liter flask adapted for introduction of materials below the surface of a reaction mixture and with wired stoppers for pressure reactions in a Glass-Col mantle, there was added 1600 ml of a solution of ammonium hydroxide (28–30% NH$_3$) and the solution heated to 100°–110° C.

To the flask, and under the liquid surface, there was then added 400 ml (6.076 mols) of acrylonitrile at 90° C. over a period of 2 hours. Heating was continued for an additional hour after addition was complete, the temperature was reduced to 80° C. and the reaction vessel prepared for stripping off unreacted ammonia.

stirrer and a reflux condenser, was added 2.3084 mols of 98% calcium chloride dissolved in a commercially available denatured ethanol. The amount of the ethanol was carefully calculated so as to form an azeotrope with the water remaining in the reaction mixture of Step 2 (95.6 ml ethanol with 4.4 ml H$_2$O). It was determined that 720 ml of ethanol was required. The ethanolic solution of the calcium chloride was admixed with the product of Step 2 and the temperature raised to 60°–65° C. and held there for 1 hour with stirring.

Step 4. Distillation of Water-Ethanol Azeotrope

The reflex condenser was replaced by a distillation head and the water-ethanol azeotrope was distilled off at a temperature of 78.2° C. When this distillation was complete, as shown by Carl-Fischer analysis, heating was continued at about 79° to 80° C. to drive off the residual ethanol. The contents of the flask, 2.308 mols of calcium Beta-alanine and sodium chloride was then dissolved in 1200 ml of methyl alcohol and heated with stirring on a water bath at 40° C.

Step 5. Formation of dl-Calcium Pantothenate

A commercially available dl-pantolactone was re-distilled at 120° C. in vacuum, 4.6168 mols of the material was dissolved in 850 ml of methanol and heated, with stirring, to 65° C. (70% solution of dl-pantolactone).

This solution was then added to the anhydrous calcium Beta-alaninate from Step 4 and heated, with stirring, to 65° C. for 12 hours. At the end of this time the reaction was completed, thin layer chromatography indicating that no pantolactone was present.

The syrupy product contaning sodium chloride was taken up in methanol, cooled and the crystalline sodium chloride filtered off. The clear filtrate was then treated to remove the methanol, and assay showed a yield of 95.3% of dl-calcium pantothenate, based on the amount of dl-pantolactone and calcium beta-alaninate starting materials.

To summarize briefly, this invention relates to an improved process for the preparation of the calcium salt of pantothenic acid. The process involves the steps of (1) reacting together acrylonitrile and ammonia to form Beta-aminopropionitrile, (2) hydrolysis to form the sodium salt of beta-alanine, (3) double decomposition to the calcium salt of betaalanine, (4) distillation of an ethanol-water azeotrope to form an anhydrous calcium salt of beta-alanine, and (5) the reaction of the anhydrous salt with dl-pantolactone to form calcium pantothenate.

In step 1 the ammonia used is preferably ammonium hydroxide of a 20–30% ammonia content and the reaction is carried out at a temperature of from about 100°–110° C. for from 5 to 10 hours, preferably about 3 hours.

The hydrolysis of the beta-aminopropionitrile to the sodium salt of beta-alanine, step 2 of the improved process, is carried out at about 65° to 95° C. for from about 1 to 4 hours, preferably 80° C. for about 1 hour. It is important in this step to use from about 10 to 15% excess of sodium hydroxide to insure completion of the hydrolysis.

In step 3 a substantially pure ethanolic solution of calcium chloride is reacted with the sodium salt of beta-alanine at a temperature of about 60° to 70° C. for from 0.5 to 3 hours, preferably about 1 hour. The excess sodium hydroxide is then neutralized with 1 N hydrochloric acid. The amount of the ethanol used in this reaction step is carefully determined so as to assure that enough is present to completely azeotrope with the water remaining in the reaction mixture so that after azeotrope distillation there remains a substantially anhydrous calcium salt of betaalanine. This azeotropic distillation is carried out in step 4. The final reaction of the process, step 5, is the direct reaction between the anhydrous calcium salt of beta-alanine and dl-pantolactone. This reaction is carried out at about 55° to about 65° C. for from 6–9 hours. The reaction product is then cooled, any precipitated sodium chloride is filtered, methanol removed and the product dried.

What is claimed is:

1. An improved process for the preparation of the calcium salt of pantothenic acid which comprises the steps of
   reacting acrylonitrile with ammonia in aqueous solution to from beta-aminopropionitrile;
   hydrolysis of beta-aminopropionitrile in the presence of sodium hydroxide to form the sodium salt of beta-alanine;
   reacting the sodium slat of beta-alanine with calcium chloride in a liquid which will from an azeotropic mixture with water to form the calcium salt of beta-alanine;
   removing water from the reaction mixture by azeotropic distillation to form an anhydrous calcium salt of beta-alanine; and
   reacting the anhydrous calcium salt of beta-alanine with dl-pantolactone to form dl-calcium pantothenate.

2. An improved process according to claim 1 wherein sufficient ethanol is used for the reaction of step three to completely azeotrope and water present.

3. An improved process for the preparation of dl-calcium pantothenate which comprises the steps of
   reacting acrylonitrile with an aqueous ammonia containing from about 28–38% ammonia at a temperature of from about 100° to 110° for about 5 to about 10 hours and thereafter removing unreacted ammonia and water from the reaction mixture and distilling the beta-aminopropionitrile so formed;
   admixing aqueous sodium hydroxide and the said distilled beta-aminopropionitrile and maintaining the mixture at a temperature of from about 65° to about 85° C. for from 2 to 4 hours and thereafter neutralizing any excess sodium hydroxide present to form the sodium salt of beta-alanine;
   reacting said sodium salt with calcium chloride in ethanol at a temperature of from about 60° to about 70° C. for from 0.5 to 3.0 hours to form sodium chloride and the calcium salt of beta-alanine;
   removing any water present by distillation of the water-ethanol azeotrope and thereafter removing residual ethanol to form anhydrous calcium beta-alaninate;
   reacting the anhydrous calcium beta-alaninate with dl-pantolactone in methanol at a temperature of from about 55° to about 65° C. for from about 6 to about 9 hours and therafter cooling and filtering the reaction product and removing methanol to obtain dl-calcium pantothenate.

* * * * *